US009830673B2

(12) United States Patent
Carlsgaard et al.

(10) Patent No.: US 9,830,673 B2
(45) Date of Patent: Nov. 28, 2017

(54) SYSTEM PORTAL CONTROL FOR A DIABETES MANAGEMENT SYSTEM

(71) Applicant: Roche Diagnostics Operations, Inc., Indianapolis, IN (US)

(72) Inventors: Eric S. Carlsgaard, Zionsville, IN (US); Aaron H. Dinwiddie, Cicero, IN (US); Igor Gejdos, Indianapolis, IN (US); Michael L. Long, Noblesville, IN (US); Teresa J. Oelmann, Noblesville, IN (US)

(73) Assignee: Roche Diabetes Care, Inc., Indianapolis, IN (US)

( * ) Notice: Subject to any disclaimer, the term of this patent is extended or adjusted under 35 U.S.C. 154(b) by 813 days.

(21) Appl. No.: 14/172,585

(22) Filed: Feb. 4, 2014

(65) Prior Publication Data

US 2014/0324464 A1  Oct. 30, 2014

Related U.S. Application Data

(60) Provisional application No. 61/816,636, filed on Apr. 26, 2013.

(51) Int. Cl.
*G06Q 50/22* (2012.01)
*G06F 19/00* (2011.01)

(52) U.S. Cl.
CPC ........... *G06Q 50/22* (2013.01); *G06F 19/322* (2013.01); *G06F 19/3406* (2013.01)

(58) Field of Classification Search
CPC ...... G06Q 50/22; G06Q 50/24; G06F 19/322; G06F 19/323–19/327

(Continued)

(56) References Cited

U.S. PATENT DOCUMENTS 6,368,273 B1  4/2002  Brown
6,442,432 B2  8/2002  Lee
(Continued)

FOREIGN PATENT DOCUMENTS

WO   2004070546 A2   8/2004

OTHER PUBLICATIONS

ZOHO CRM, Activating and Deactivating Users, Dec. 25, 2012, 3 pages.*

(Continued)

*Primary Examiner* — Luke Gilligan
*Assistant Examiner* — Jason Tiedeman
(74) *Attorney, Agent, or Firm* — Harness Dickey

(57) ABSTRACT

A computer-implemented method for managing accounts in a diabetes management system. The method includes receiving, by an account manager, a request to deactivate a first account associated with a healthcare provider. The first account may be associated with a plurality of patient accounts. The account manager may be implemented as computer executable instructions executing on a computer processor of a server device. The method includes removing, by the account manager, access to data associated with the first account. Each of the patient accounts associated with the first account are identified and may be deactivated by the account manager. An electronic notification may be sent to a person associated with each of the identified patient accounts, advising the person that the corresponding patient account has been deactivated. An audit record may be created in a data store, the audit record indicating the deactivation of the first account.

19 Claims, 11 Drawing Sheets

(58) Field of Classification Search
USPC .......................................................... 705/2, 3
See application file for complete search history.

(56) References Cited

U.S. PATENT DOCUMENTS

| | | | |
|---|---|---|---|
| 6,589,169 B1 | 7/2003 | Surwit et al. | |
| 7,103,578 B2 | 9/2006 | Beck et al. | |
| 7,188,151 B2 | 3/2007 | Kumar et al. | |
| 7,463,930 B2 | 12/2008 | Housworth et al. | |
| 8,615,532 B2 | 12/2013 | Bessette | |
| 8,630,952 B2 * | 1/2014 | Menon | G06Q 20/20 705/44 |
| 8,666,807 B1 * | 3/2014 | Murray | G06Q 30/0241 705/14.4 |
| 2002/0016718 A1 | 2/2002 | Rothschild et al. | |
| 2002/0016721 A1 | 2/2002 | Mason et al. | |
| 2003/0217159 A1 | 11/2003 | Schramm-Apple et al. | |
| 2004/0148259 A1 * | 7/2004 | Reiners | G06Q 20/02 705/42 |
| 2004/0167465 A1 | 8/2004 | Mihai et al. | |
| 2006/0004603 A1 * | 1/2006 | Peterka | G06Q 10/00 705/2 |
| 2006/0010098 A1 * | 1/2006 | Goodnow | G06F 19/322 |
| 2006/0036555 A1 | 2/2006 | Beck et al. | |
| 2006/0184524 A1 | 8/2006 | Pollanz | |
| 2007/0100222 A1 | 5/2007 | Mastrototaro et al. | |
| 2007/0192137 A1 * | 8/2007 | Ombrellaro | G06Q 50/22 705/2 |
| 2007/0192493 A1 * | 8/2007 | Manolache | G06Q 10/107 709/226 |
| 2008/0004904 A1 | 1/2008 | Tran | |
| 2008/0071580 A1 | 3/2008 | Marcus et al. | |
| 2008/0101597 A1 | 5/2008 | Nolan et al. | |
| 2008/0127310 A1 * | 5/2008 | Robbins | G06F 21/6245 726/4 |
| 2008/0140162 A1 | 6/2008 | Goetz et al. | |
| 2008/0154099 A1 | 6/2008 | Aspel et al. | |
| 2008/0301158 A1 * | 12/2008 | Brown | G06Q 50/22 |
| 2010/0191824 A1 * | 7/2010 | Lindsay | G06F 19/3406 709/217 |
| 2010/0223184 A1 * | 9/2010 | Perlman | G06Q 20/04 705/44 |
| 2010/0324934 A1 | 12/2010 | Selinfreund et al. | |
| 2011/0159921 A1 * | 6/2011 | Davis | H04M 1/72569 455/556.1 |
| 2012/0240060 A1 * | 9/2012 | Pennington | G06F 1/1618 715/753 |
| 2012/0278094 A1 * | 11/2012 | Kovacevic | G06Q 50/22 705/2 |
| 2013/0059541 A1 * | 3/2013 | Sloan | G06Q 50/24 455/41.2 |
| 2013/0229288 A1 | 9/2013 | Alexander et al. | |
| 2013/0289889 A1 * | 10/2013 | Yuen | G06F 19/3418 702/19 |
| 2013/0305057 A1 * | 11/2013 | Greco | G06F 21/80 713/189 |

OTHER PUBLICATIONS

Medtronic—Getting Started—CareLink Personal Software (2011); XP055081464; URL: http://www.medtronic-diabetes.com.au/wcm/groups/mdtcom_sg/@mdt/@ap/@au/@diabetes/documents/documents/contrib_107976.pdf (retrieved on Sep. 27, 2013), 11 pages.

* cited by examiner

SYSTEM PORTAL CONTROL FOR A DIABETES MANAGEMENT SYSTEM

CROSS-REFERENCE TO RELATED APPLICATIONS

This application claims the benefit of U.S. Provisional Application No. 61/816,636, filed on Apr. 26, 2013. The entire disclosure of the above application is incorporated herein by reference.

FIELD

The present disclosure relates to portal control features that pertain to a diabetes management system.

BACKGROUND

This section provides background information related to the present disclosure which is not necessarily prior art.

Persons with diabetes often have difficulty regulating blood glucose levels in their bodies. As a consequence, many of these persons carry specialized electronic meters, called blood glucose meters, which allow them to periodically measure their glucose levels and take appropriate action, such as administering insulin. After a blood glucose measurement or series of measurements is taken, a diabetic patient may find it useful to communicate these measurements to his or her healthcare professional for further review and analysis. In this regard, the patient's blood glucose meter may be capable of storing the blood glucose measurements for later review and analysis by the patient or the healthcare professional, who may then record the measurements manually or electronically.

The process of measuring, storing, recording and analyzing blood glucose levels can be a very time consuming process for both the patient and the patient's healthcare professional. Often, the exchange and review of data requires a meeting between the patient and the healthcare professional. People with diabetes are often searching for better and more efficient ways to manage their health. In addition, healthcare professionals need new tools to motivate people with diabetes to communicate more effectively. Technology can provide a viable platform for software applications for a wide variety of consumer demands. Moreover, many people with diabetes use personal computers and/or mobile devices in their daily lives.

In order to improve the effectiveness and efficiency of storing, communicating and analyzing blood glucose measurements, it may be desirable for the patient and the patient's healthcare professional to send data, including blood glucose measurements, to a centralized electronic data repository for later retrieval and analysis. It is further desirable for the patient and the patient's healthcare professional to have these data transmission capabilities at various times and from various locations. The sharing of data and the data repository can be managed by administrative guidelines. Such administrative guidelines may need to follow certain procedures for opening, closing, and deactivating both patient and healthcare provider accounts associated with the data sharing and storage.

SUMMARY

This section provides a general summary of the disclosure, and is not a comprehensive disclosure of its full scope or all of its features.

The present disclosure provides a computer-implemented method for managing accounts in a diabetes management system. The system can include receiving, by an account manager, a request to deactivate a first account associated with a healthcare provider. The first account may be associated with a plurality of patient accounts. The account manager may be implemented as computer executable instructions executing on a computer processor of a server device. In various aspects, the method can include removing, by the account manager, access to data associated with the first account. Each of the patient accounts associated with the first account are identified by the account manager and deactivated. An electronic notification may be sent by the account manager to a person associated with each of the identified patient accounts. The electronic notification may advise the person that the corresponding patient account has been deactivated. The method may include creating, by the account manager, an audit record in a data store, where the audit record indicates the deactivation of the first account.

In various other aspects, the computer-implemented method for managing accounts in a diabetes management system comprises receiving, by an account manager, a request to deactivate a patient account associated with the diabetes care management system. The account manager may be implemented as computer executable instructions executing on a computer processor of a server device. The account manager may provide a warning notification indicating active sessions of the patient account will be terminated. The method can include soliciting, by the account manager, a confirmation of the request to deactivate the patient account. The patient account may be deactivated upon receipt of the confirmation of the request to deactivate the patient account. The account manager may send an electronic notification to a person associated with the patient account, where the electronic notification advises the person that the corresponding patient account has been deactivated. The method can include creating, by the account manager, an audit record in a data store, where the audit record indicates the deactivation of the patient account.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Example embodiments will now be described more fully with reference to the accompanying drawings.

Figure 1:
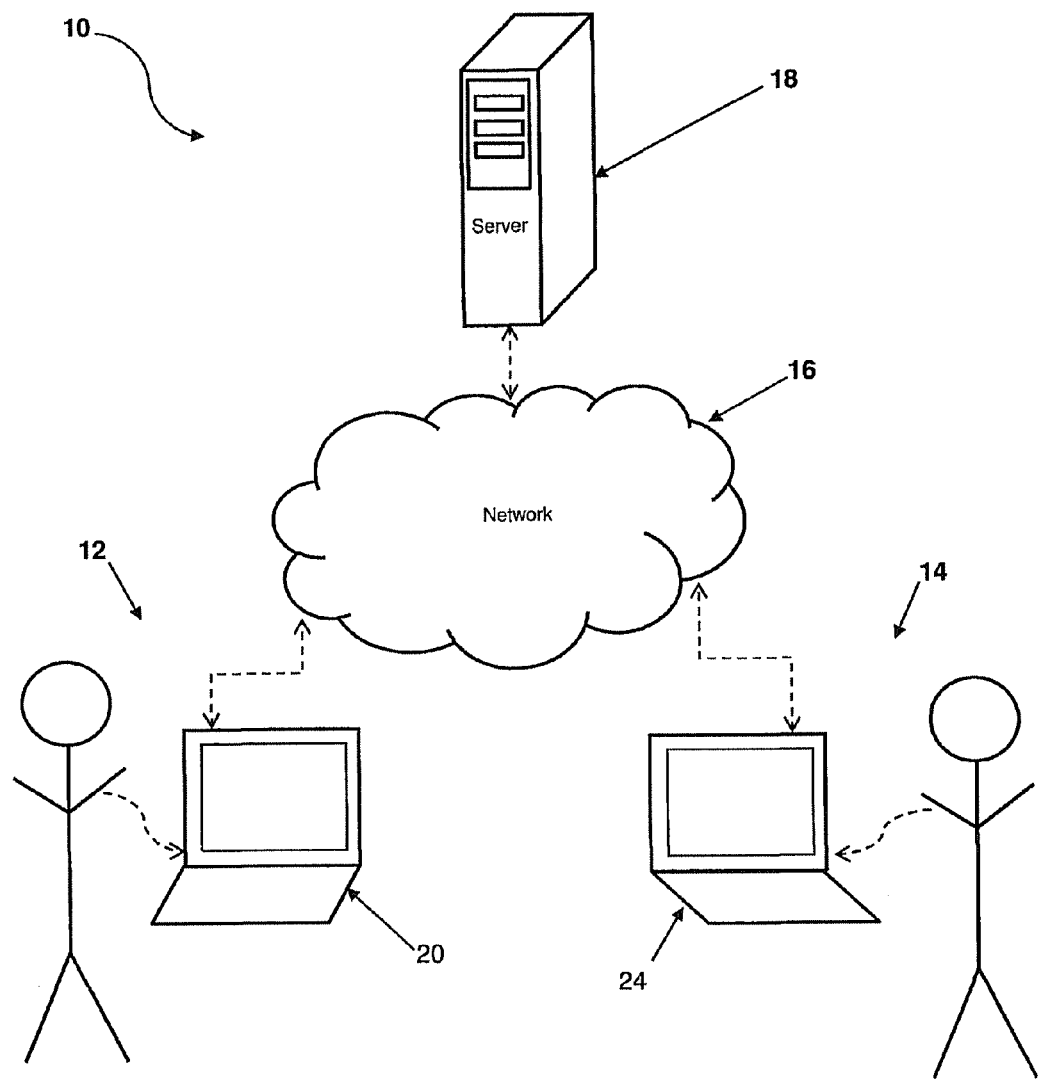
FIG. 1 is a diagram depicting an exemplary diabetes management system.

FIG. 1 illustrates an exemplary diabetes management system ("DMS") 10 for storing and transmitting medical data and information across a distributed computing environment. By way of non-limiting example, such data and information might include blood glucose measurements, search engine functionality, alerts and reminders, user-entered notes, reports and graphs, and global positioning system information.

The diabetes management system 10 may include generally a patient data system 12, a healthcare professional data system 14, a network 16, and at least one server computer 18. As will be explained in more detail below, the diabetes management system 10 may be configured such that data and information is electronically sent and received to and from the patient data system 12, the healthcare professional data system 14, and the server computer 18 via the network 16.

Figure 3:
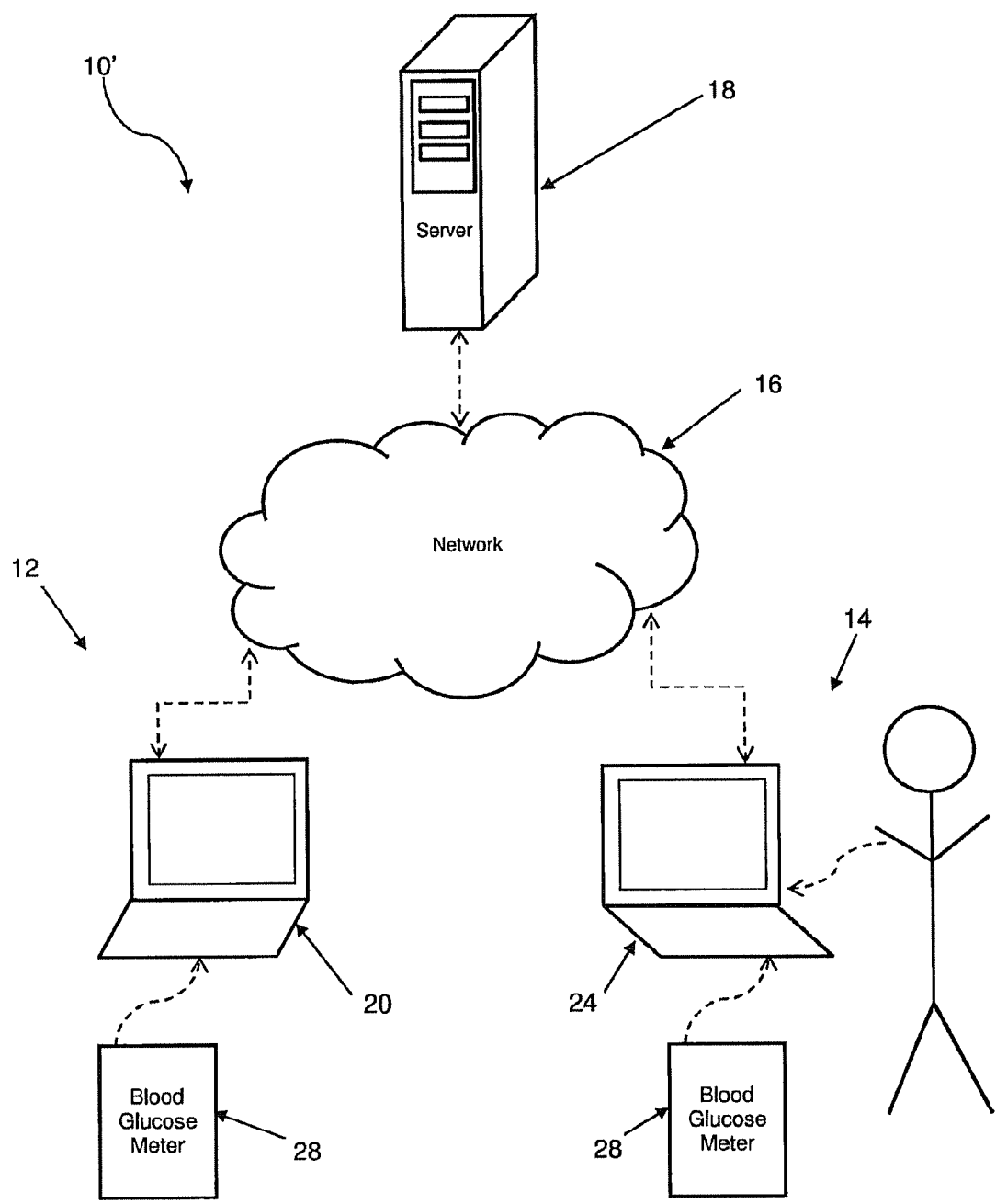
FIG. 3 is a diagram depicting an alternative embodiment of the diabetes management system.

The diabetes management system 10' illustrated in FIG. 3 may also generally include a medical data recording device 28, such as a blood glucose meter, for measuring and storing certain medical data or information, such as blood glucose measurements. The medical data recording device 28 may be operable to send medical data or information to at least one of the patient computing device 20 and the healthcare professional computing device 24 through a data transmission device, such as a hard-wired data port or a wireless data port such as a Bluetooth receiver, incorporated therein. The medical data recording device 28 may be associated with a unique identifier or security code that attaches to any data transmitted by the medical data recording device. Accordingly, in this method of data transmission, the patient or other user may not be required to enter a username, password, or other security code prior to transmitting data via the network 16.

The patient data system 12 may include at least one patient computing device 20 operably connected to, and in communication with, the network 16 through a wired or wireless connection such as WiFi. By way of example, the patient computing device 20 may be a desktop computer or a mobile communication device such as an electronic tablet or a smartphone. The patient computing device 20 may include a data input device, a processor, a memory, and an output device. The data input device may be a touchscreen, a keyboard, a mouse, a microphone, a hard-wired data port such as a universal serial bus port, or a wireless data port such as a Bluetooth receiver. The processor may be connected to the data input device, the memory, and the output device. In an example embodiment, the processor includes a general purpose processor. In another example embodiment, the processor includes an application specific integrated circuit. The output device includes a display, a speaker, or the like.

Figure 2:
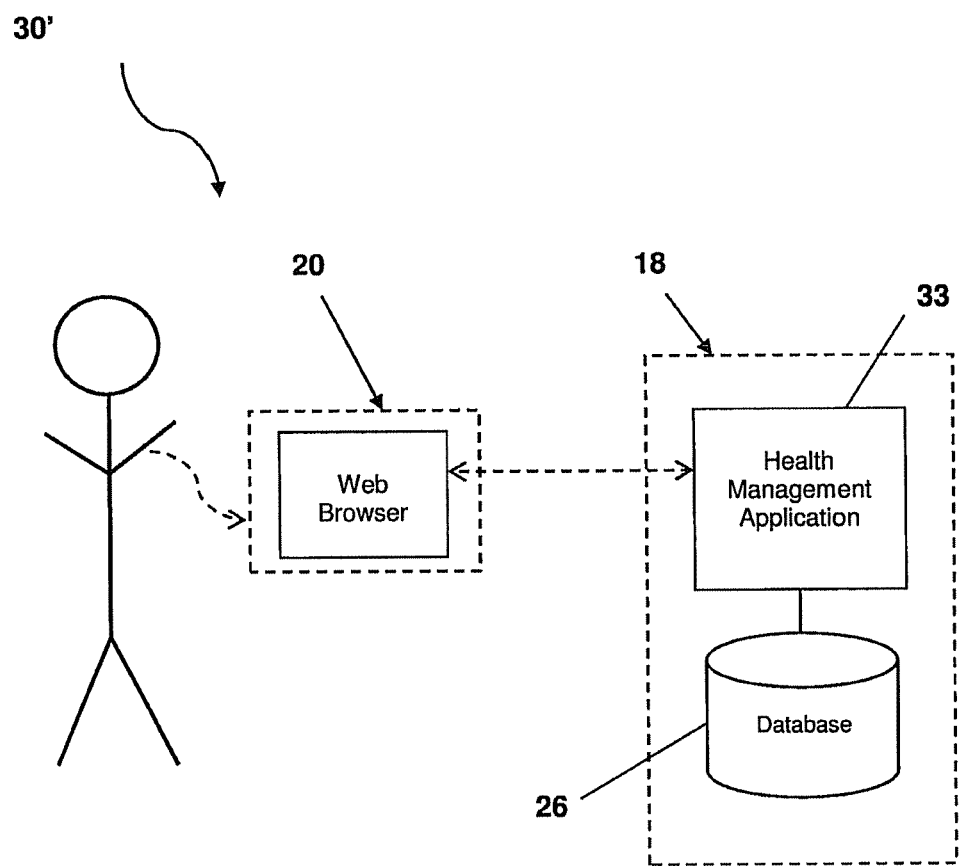
FIG. 2 is a diagram depicting a software architecture system for the diabetes management system.

With reference to FIGS. 1 and 2, in one embodiment of the patient data system 12, a user (e.g., a patient) may enter data or information such as blood glucose measurements into a web browser on the patient computing device 20 via the data input device for transmittal via the network 16. Prior to entering or transmitting data via the network 16, the user may be required to enter a username, password, or other security code, in order to ensure the accurate transmission and storage of data, as will be described in more detail below.

The healthcare professional data system 14 may include at least one healthcare professional computing device 24 operably connected to, and in communication with, the network 16 through a wired or wireless connection, such as WiFi. A physician or other person with access to the healthcare professional computing device 24 may utilize the network 16 to download and view data or information such as blood glucose measurements that are stored on the server computer 18. By way of example, the healthcare professional computing device 24 may be a desktop computer or a mobile communication device such as an electronic tablet or a smartphone. The healthcare professional computing device 24 may include a data input device, a processor, a memory, and an output device. The data input device may be a touchscreen, a keyboard, a mouse, a microphone, a hard-wired data port such as a universal serial bus port, or a wireless data port such as a Bluetooth receiver. The processor may be connected to the data input device, the memory, and the output device. In an example embodiment, the processor includes a general purpose processor. In another example embodiment, the processor includes an application specific integrated circuit. The output device includes a display, a speaker, or the like.

With reference to FIGS. 1 and 2, the server computer 18 may include a processor, an input device, an output device, and a memory including a database 26. The processor is connected to the memory, the input device, and the output device. In an example embodiment, the processor includes a general purpose processor. In another example embodiment, the processor includes an application specific integrated circuit. The input device includes a keyboard, a mouse, a touchpad, a trackpad, or the like. The output device includes a display, a speaker, or the like. The server computer 18 and database 26 may be operably connected to, and in communication with, the network 16 through a wired or wireless connection. The server computer 18 may be operable to send and receive via the network 16 data, such as blood glucose measurements received from the patient data system 12, to the database 26 for storage and later retrieval. As will be discussed below, data and information sent via the network 16 may be assigned to a unique patient account prior to being stored in the database 26 located on the server computer 18.

FIG. 3 illustrates an alternative embodiment of the diabetes management system 10'. The alternative embodiment of the diabetes management system 10' shown in FIG. 3 may be similar to the embodiment shown in FIG. 1, and include a patient data system 12, a healthcare professional data system 14, a network 16, and at least one server computer 18. The patient data system 12 may include at least one patient computing device 20 operably connected to, and in communication with, the network 16 through a wired or wireless connection such as WiFi. The healthcare professional data system 14 may include at least one healthcare professional computing device 24 operably connected to, and in communication with, the network 16 through a wired or wireless connection, such as WiFi, through which a physician or other person with access to the healthcare professional computing device may download and view data or information such as blood glucose measurements sent from the patient computing device 20 via the network 16.

The medical data recording device 28 may be configured to transmit data to at least one of the patient computing device 20, the healthcare professional computing device 24, and the server computer 18 at regular, programmable intervals, at varying times chosen by the user, in real time as blood glucose measurements are taken, or when blood glucose measurements reach certain threshold levels that may be set by the patient or the healthcare professional.

Figure 4:
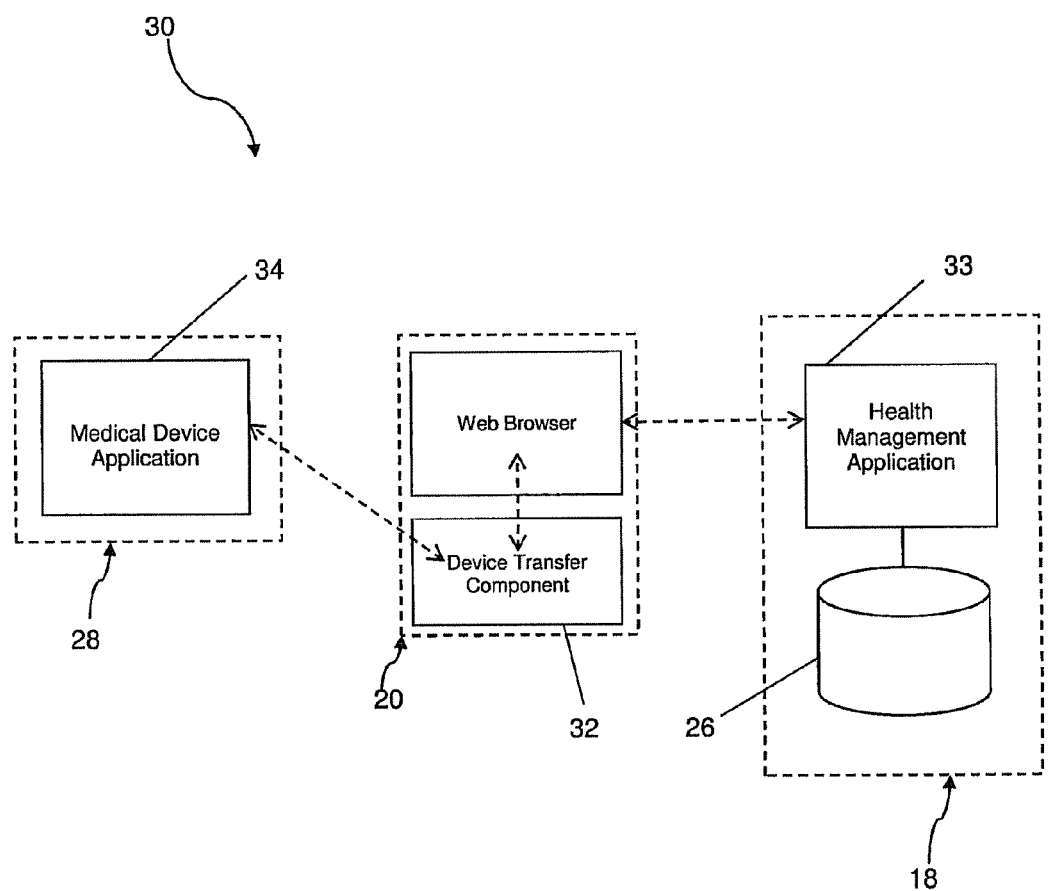
FIG. 4 is a diagram depicting an alternative embodiment of the software architecture system for the diabetes management system shown in FIG. 3.

With reference to FIG. 4, one embodiment of a software architecture system 30 for use with the diabetes management system 10 is illustrated. The software architecture system 30 may be operable to allow transmission and manipulation of data and information, such as blood glucose measurements, from the medical data recording device 28, through the network 16 and between the patient data system 12, the server computer 18, and the healthcare professional data system 14.

The software architecture system 30 may include a device transfer component 32. The device transfer component 32 may be stored on the server computer 18 for transmission through the network 16 and installation on the patient computing device 20 and the healthcare professional computing device 24. Installation of the device transfer component 32 onto the patient computing device 20 or the healthcare professional computing device 24 will allow such device to send data and information, such as blood glucose measurements, to the health management application 33 installed on the server computer 18. When the medical data recording device 28 sends data to the patient computing device 20 or the healthcare professional computing device 24, the device transfer component 32 is operable to pass the data to the server computer 18 via the network 16, without storing the data in the device transfer component 32 or the patient computing device 20. A medical device application 34 may be installed on the medical data recording device 28, to facilitate the exchange of data and information with the device transfer component 32, as described above. Data sent via the device transfer component 32 may include an identifier code unique to the particular patient and/or medical data recording device 28 from which it was received. The identifier code may allow the device transfer component 32 and the database 26 to efficiently send, store, and retrieve data from unique locations, or patient accounts, within the database 26.

Prior to transferring data and information through the network 16, a user may be required to link or associate the medical data recording device 28 with a unique patient account created on the server 18. Authentication may be accomplished by first allowing the medical data recording device 28 to communicate with a patient computing device 20 via an input device such as a USB port or a Bluetooth receiver. The medical data recording device 28 may be assigned a unique identification code or authentication token. After downloading and running the device transfer component 32, and allowing the medical data recording device 28 to communicate with the personal computing device 20, the medical data recording device's authentication token can be assigned to the appropriate patient account. Once the medical data recording device's 28 authentication token has been assigned to the patient account, data and information can be transferred through the device transfer component 32 and assigned to the appropriate patient account in the database 26.

In an alternative embodiment of the data transfer process, the device transfer component 32 may be assigned a unique identification code. Prior to transferring data and information from a medical data recording device 28 through the network 16, the user may be required to associate the device transfer component's 32 unique identification code with the patient's account. Data and information from the medical data recording device 28 can be linked to the device transfer component's 32 unique identification code prior to transmission through the network, and thus assigned to the appropriate patient account in the database 26.

After data has been transferred from the device transfer component 32 to the patient account located on the server 18, the software architecture system 30 may allow such data to be further transferred from the patient account to authorized health professional computing devices 24 and patient computing devices 20 via the device transfer component 32. Transfer of data from the patient account located in the database 26 on the server 18 may require linking the patient account with the device transfer component 32 installed on the health professional computing device 24.

The software architecture system 30 may also allow a patient, healthcare professional, or other user to create customized reports related to the data and information contained therein or perform research with respect to information contained within or outside of the software architecture system. In addition, the software architecture system 30 may be operable to provide data backup and restoration services with respect to data and information that may have been lost from the patient data system 12 or the healthcare professional data system 14.

With reference to FIG. 2, in another embodiment of the software architecture system 30', the user may send and receive data from the server computer 18 and the database 26 via a web browser on the patient computing device 20, in lieu of downloading and utilizing the device transfer component 32 on the patient computing device. In the software architecture system 30', the server computer 18 may include the device transfer component 32, allowing the user to send data and information to the server computer 18 for storage in the database 26, and for further transmission to the healthcare professional computing device 24 via the network 16. The user may access the diabetes management system 10 and the software architecture system 30' by entering a URL designated for the diabetes management system directly into a web browser.

Prior to transferring data through the network 16 to the server computer 18, the user may be required to create a unique patient account and security credentials, such as a username and password, to ensure a unique and secured storage location in the database 26. The user may also be required to associate, or link, the medical data recording device 28 authentication token with the patient account. Once the user has created the patient account and linked the medical data recording device 28 authentication code to the patient account, the user may be permitted to transfer data and information to and from the server computer 18 without otherwise logging into the patient account. In one aspect of the diabetes management system 10, access to the server 18 via the web browser may allow a user to transmit data such as blood glucose measurements, patient weight, meal information, and similar information, to the patient account in the database 26. In another aspect of the diabetes management system 10, access to the server 18 via the web browser may allow the user to create and view reports, graphs, and other information based at least in part on data transmitted from the user.

Communication between the patient data system 12, the healthcare professional data system 14, and the server computer 18 may utilize HTTP basic authentication in combination with secure sockets layer (SSL) security protocol. Other communication and security protocols known in the art are also contemplated.

Operation of the diabetes management system 10 may include a user operating a web browser to access the server computer 18 via the network 16. For example, a user may create a unique patient account on the server computer 18 utilizing security credentials such as a username and password. Creation of a patient account may allow the user to send and store data and information in a secure location within the database 26 on the server computer 18.

In other aspects, a user may operate a web browser to access the server computer 18 in order to download the device transfer component 32 onto at least one patient computing device 20 and/or at least one health professional computing device 24.

A user may register the medical data recording device 28 with at least one of the device transfer component 32 and the patient account. Registration of the medical data recording device 28 with the device transfer component 32 and the patient account may be accomplished by allowing the medical data recording device 28 to communicate with a patient computing device 20 via an input device such as a USB port, a Bluetooth receiver, or other wired or wireless technology. Each medical data recording device 28 may be assigned a unique identification code or authentication token that can be associated with the patient account, thus ensuring that data and information sent from the medical data recording device 28 is stored only in the patient account. It is also contemplated that registration of the medical data recording device 28 with the device transfer component 32 and the patient account may be accomplished by the user directly entering the medical data recording device's identification code or authentication token directly into device transfer component 32 or a web browser.

In various aspects, a user may send data and information from the medical data recording device 28 to the device transfer component 32. Data and information may be sent via an input device such as a USB port or a Bluetooth receiver on the patient computing device 20 or the health professional computing device 24. Data and information received from the medical data recording device 28 may include the identification code or authentication token assigned to the particular medical data recording device. In this way, the diabetes management system 10 can ensure the integrity of data and information sent to the patient account.

The device transfer component 32 may send data and information received from the medical data recording device 28 to the server 18. In certain aspects, it is contemplated that the device transfer component 32 may not necessarily store or otherwise record in memory the data and information received from the medical data recording device 28. Rather, the device transfer component 32 may function as an intermediary between the medical data recording device 28 and the server 18, facilitating the transfer of data and information therebetween. Data and information transferred from device transfer component 32 may be authenticated and directed to the patient account through the associated identification code or authentication token received from the medical data recording device 28, as explained above.

Data and information associated with the patient account in the server computer 18 database 26 may be transferred to at least one of the patient computing device 20 and the health professional computing device 24 via the network 16. The transfer of data from the server computer 18 may first require authentication.

In various aspects, the present technology provides a web-portal by which the owners of the diabetes management system perform various functions related to healthcare provider accounts, patient accounts, or both. In other aspects, a web browser or web-based application may be used to perform similar functions. For example, a healthcare provider may be set up with a first, or main account to help manage treatment of a plurality of different patients, each of which has a respective patient account accessible from the server computer 18 associated with the diabetes management system. The healthcare provider may be able to configure its account to display certain data, statistics, and/or usage data from the various patients having patient accounts accessible through the healthcare provider's account. A review of the data may allow the healthcare provider to better assess the patients' health, and adjust treatment regimens based on the recent and historical data.

By utilizing the diabetes management system 10, healthcare providers and patients may readily store, share, and later access medical information relating to the patients, for example, to analyze historical information regarding a subject's biological condition, operation of the patient's portable medical device 28, treatment, treatment results, personal habits, or the like. Based on such historical data, the healthcare provider and/or patient may be able to recognize trends, beneficial practices, detrimental practices or the like and, thereby, adjust or design treatment plans that take advantage of beneficial trends and practices and avoids detrimental trends and practices.

The diabetes management system 10 may include software for generating or otherwise providing reports containing information received from a patient, a group of patients, or multiple groups of patients within the same healthcare provider account. In this manner, a patient or a patient's healthcare provider may readily access formatted reports of information regarding the patient's condition, historical condition, the patient portable medical device operation or condition, or the like, or similar information regarding one or more defined groups of patients. Reports may be formatted in various pre-defined formats provided by the diabetes management system 10. Alternatively or in addition, the system 10 may allow patients and/or healthcare providers to design their own report format, including determining what type of information to include in the report and how the information is filtered, presented, displayed, etc. Various aspects of the present disclosure are directed a comprehensive system capable of collecting and managing patient information for multiple patients, the multiple patients with a plurality of different types of medical devices.

The sharing of accounts and data, as well as the maintaining of a suitable data repository can be managed by various administrative guidelines. Such administrative guidelines may need to follow certain procedures for opening, closing, and deactivating both patient and healthcare provider accounts associated with the data sharing and storage.

Figure 5:
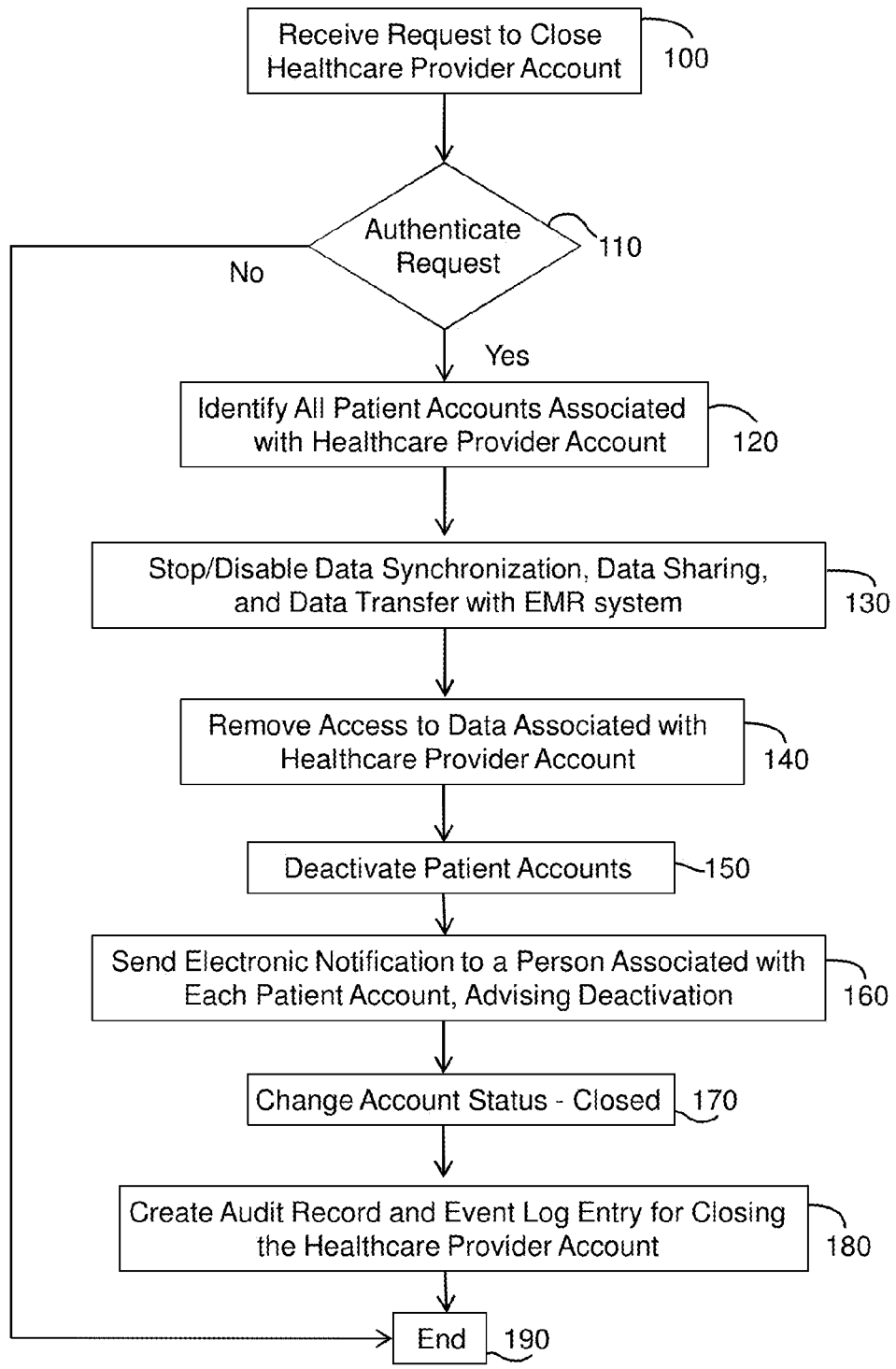
FIG. 5 is a schematic diagram illustrating various operations that may be performed in connection with the closing of a healthcare provider account associated with the diabetes management system.
Figure 6:
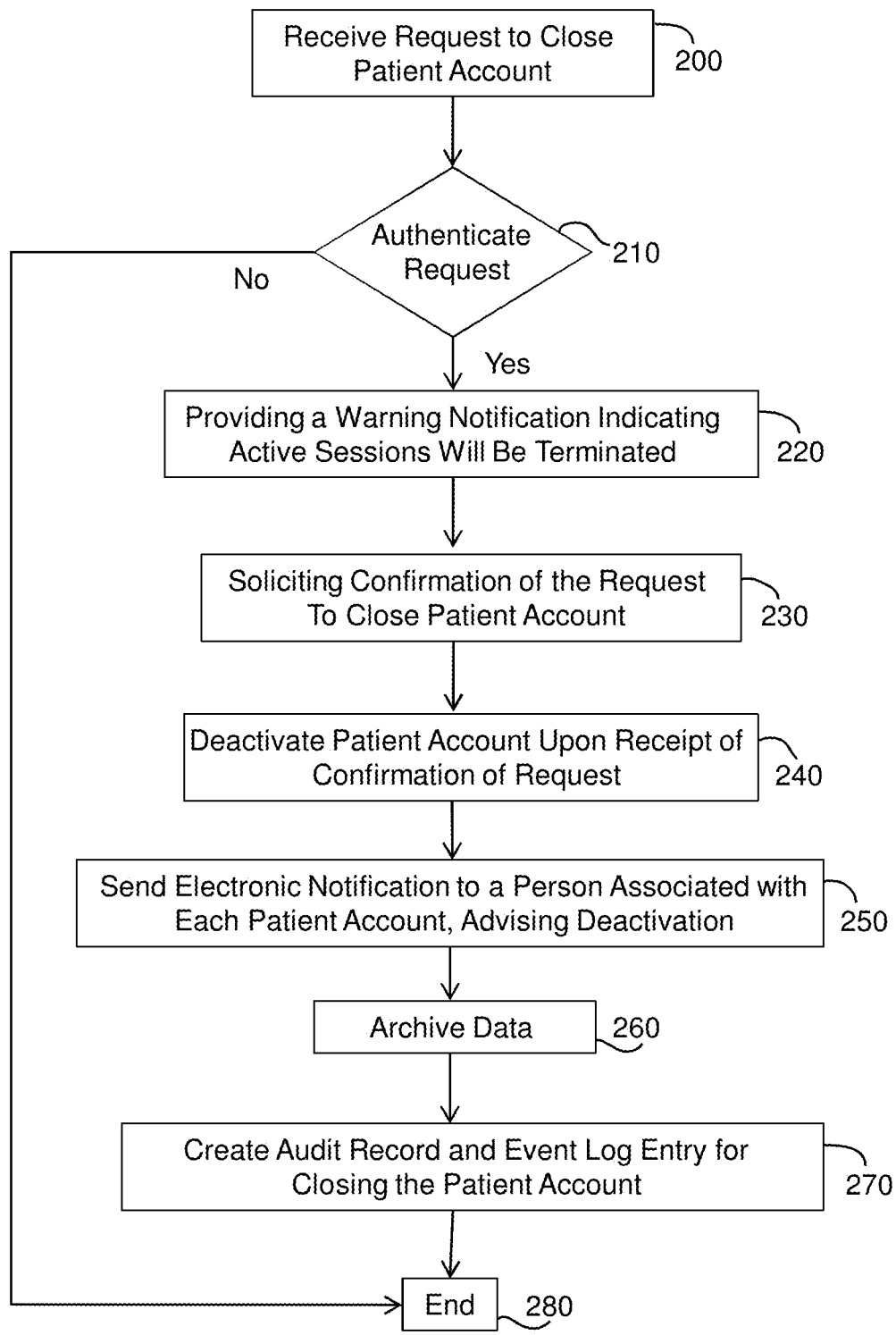
FIG. 6 is a schematic diagram illustrating various operations that may be performed in connection with the closing of a patient account associated with a healthcare provider and the diabetes management system.

With general reference to FIGS. 5 and 6, the web-portal or web-based browser/applications by which either the owners of the diabetes management system or the healthcare providers themselves perform various functions related to healthcare provider accounts, patient accounts, or both can be provided with certain predetermined procedures to activate and deactivate accounts, as well as link healthcare provider accounts with a plurality of patient accounts. It should be understood that FIGS. 5 and 6 are merely exemplary in nature, and are not mutually exclusive aspects. For example, certain features shown with the method represented in FIG. 5 may also be performed with the method represented in FIG. 6, and vice versa, even though they are not specifically shown. Further, not each feature is necessarily a required step of the respective method, and the order in which the method steps are performed should not be limited to the order specifically depicted in the figures or discussed herein.

FIG. 5 generally represents one non-limiting process associated with the closure or deactivation of a healthcare provider account. As represented by method box 100, an account manager can receive a request to deactivate a first account associated with a healthcare provider, or a healthcare provider account, which in turn may be associated with a plurality of patient accounts that may be linked to the healthcare provider account. As used herein, the term "account manager" refers to the implementation of computer executable instructions executed on a computer processor of a server device, or the like. By way of example, an account manager may include a web-based portal or a web-based application, and may include various functionality to perform logic-based operations.

At various points during the deactivation or account closing process, the request may be authenticated, as represented by method box 110. Authentication may be accomplished using various techniques, including, but not limited to authentication of username and/or password credentials, permissions, unique identifiers, security questions, or other identifications. Authentication can also include various requests to one or more users seeking a confirmation or acknowledgement of the proposed request.

The healthcare provider account may generally be associated with a plurality of patient accounts that are linked by the healthcare provider or diabetes management system operator. For example, patient accounts may be provided with a unique identifier, such as a number, code, or token. At some point, the healthcare provider account would be linked together with various patient accounts by association of the healthcare provider account with the unique identifier for each patient account. Additionally or alternatively, the healthcare provider accounts may have the unique identifier. In certain aspects, associating patient accounts with the healthcare provider account may be performed by the healthcare provider using the healthcare provider computing device, or may be performed by a diabetes management system operator using a web-portal. The information associating healthcare provider accounts with patient accounts may be stored in an appropriate data store.

Once the request for deactivation or closure of a healthcare provider account is received and/or authenticated, the present technology may identify all of the patient accounts associated with the healthcare provider account as referenced by method box 120. For example, the patient accounts may be filtered out based on the associated healthcare provider account. In addition to being filtered by the healthcare provider, patient accounts can additionally be filtered by diabetes type, geographic location, age, gender, therapy type, user type, etc. As referenced by method box 130, various data synchronization activities, data sharing, and data transfers between accounts may be interrupted, stopped, and/or disabled, by the account manager, between the healthcare provider account and the diabetes management system, as well as each of the identified patient accounts. Data synchronization activities may include, but are not limited to, processes of establishing consistency among data between patient accounts and the healthcare provider account, and the continuous harmonization of the data over time. These activities may include synchronizing files; data; updates; settings; preferences; formats; statistics; usage information; device information; configurations; messages; notes; etc. In further aspects, data sharing functions may also be stopped and disabled, by the account manager, between the healthcare provider account and the identified patient accounts. Data sharing functions may include, but are not limited to, providing read and/or write functions and access to medical, usage, and personal data; bibliographic information; statistics; etc. between the healthcare provider account and the identified patient accounts and/or patient medical devices.

To the extent any data transfer activities took place between the healthcare provider account and/or patient accounts, those transfer activities may be disabled by the account manager after a request to close or deactivate an account. For example, certain healthcare provider accounts and/or patient accounts may be associated, linked, or otherwise work with electronic medical records (EMR) systems as commonly known in the art. In the event a healthcare provider account or patient account is closed or deactivated, appropriate notifications may need to be provided to EMR systems or other user interfaces as may be required to stop pending or future data transfers between the EMR systems and healthcare provider accounts and/or patient accounts, or to indicate that such accounts are no longer available for access by the EMR system.

As indicated by method boxes 140 and 150, upon receiving a request to deactivate or close a healthcare provider account, the account manager may deny or remove further access to the data associated with the healthcare provider account, and deactivate certain or all of the patient accounts associated with the healthcare provider account.

In certain aspects, the methods for managing accounts includes sending, by the account manager, an electronic notification to a person associated with each of the identified patient accounts, such as the patient, where the electronic notification advises the person that the corresponding patient account has been deactivated, and to inform them that the healthcare provider office has stopped data sharing with them. By way of example, and with reference to method box 160, the electronic notification may be via electronic mail or other electronic messaging service. As indicated by method box 170, the status of the healthcare provider account may be changed to a "closed" status, and the closure date may be recorded. Messages may be displayed to one or more users informing them that the healthcare provider account is closed and all associated patient and user accounts are deactivated. Various audit records and event log entries may be created by the account manager that can be saved and/or archived in a data store within the system, as shown by method box 180, to indicate and memorialize various information related to the closed healthcare provider and/or patient account(s). Once closed or deactivated, the web-based portal or web-based application may display a message to inform a user that various accounts are deactivated and that the user details and other identifying features can no longer be edited. It should be understood that various opportunities may be provided throughout this process enabling a user to cancel one or more operations associated with the closing of the accounts.

In additional to typical logistical and testing information generally regarded as useful for diabetes treatment and management control, the web-portal may be configured to collect and use geographic locations of the healthcare provider and/or the patients in order to comply with certain regulatory and/or compliance regimes that may exist for different geographic locations, such as different states or countries. By way of example, different geographic locations may have different requirements concerning the archiving of data related to medical treatment. In various aspects, the computer-implemented methods of the present technology can be configured to archive data associated with each of the plurality of patient accounts and healthcare provider accounts for at least a predetermined period of time. The predetermined period of time may be specifically affiliated with regulations or compliance standards for the geographic location, which may be recorded by the system for each account and managed by the owner of the diabetes management system. Various portions of the data such as references to medical patient data and personal data may be encrypted for patient security and confidentiality.

FIG. 6 generally represents one non-limiting process associated with the closure or deactivation of a patient account, where the user initiating the closure may be authenticated as a healthcare provider. As represented by method box 200, an account manager can receive a request to deactivate or close a specific patient account associated with a healthcare provider, or a healthcare provider account. The method may include various confirmations of the deactivation request or authenticate the request as previously described above and noted by method box 210.

With reference to method box 220, when a user selects to deactivate a user account, the computer-implemented system may display a warning message that any active sessions of the deactivated user will be terminated. As shown in method box 230, a specific confirmation may optionally be solicited by the account manager, seeking confirmation of the request to close the patient account. The patient account may then be deactivated and closed upon receipt of the confirmation of the request as depicted in method box 240. Similar to the method of deactivating the healthcare provider account, method box 250 indicates that an electronic notification may be sent by the account manager to a person, such as a patient, associated with the patient account to advise the person that the corresponding patient account has been or will be deactivated and/or closed. Certain data associated with the patient account may be archived as noted in method box 260. The archived data may be stored for a predetermined period of time as discussed above. Appropriate audit records and event log entries documenting the deactivation of the patient account may be created as referenced by method box 270.

In various aspects, the patient account may be associated with a portable medical device, for example, having a unique serial number or identifier associated with the account. Methods according to the present technology may include disabling, by the account manager, data transfer activities associated with the portable medical device affiliated with a closed or deactivated patient account.

FIGS. 7-11 illustrate various graphical user interfaces that may be used in connection with the diabetes management system, portal, and associated software architecture.

Figure 7:
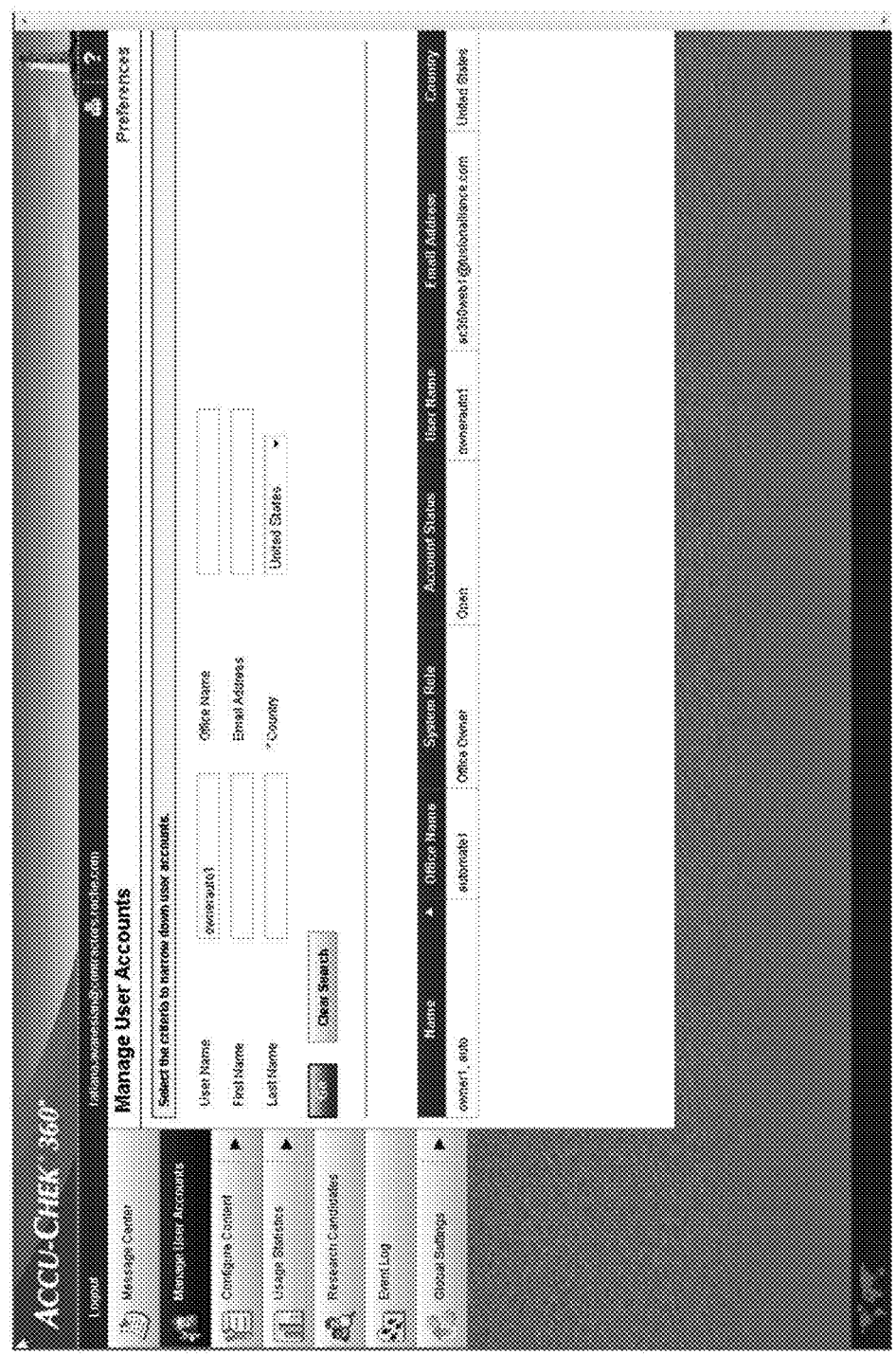
FIGS. 7-11 illustrate various graphical user interfaces that may be used in connection with the diabetes management system, portal, and software architecture.

FIG. 7 generally depicts management and viewing options for a web-portal user account. Certain criteria can be selected to narrow down the display of user accounts. By way of example, accounts can be sorted by name, office name, system role, account status, user name, associated email address, and country.

Figure 8:
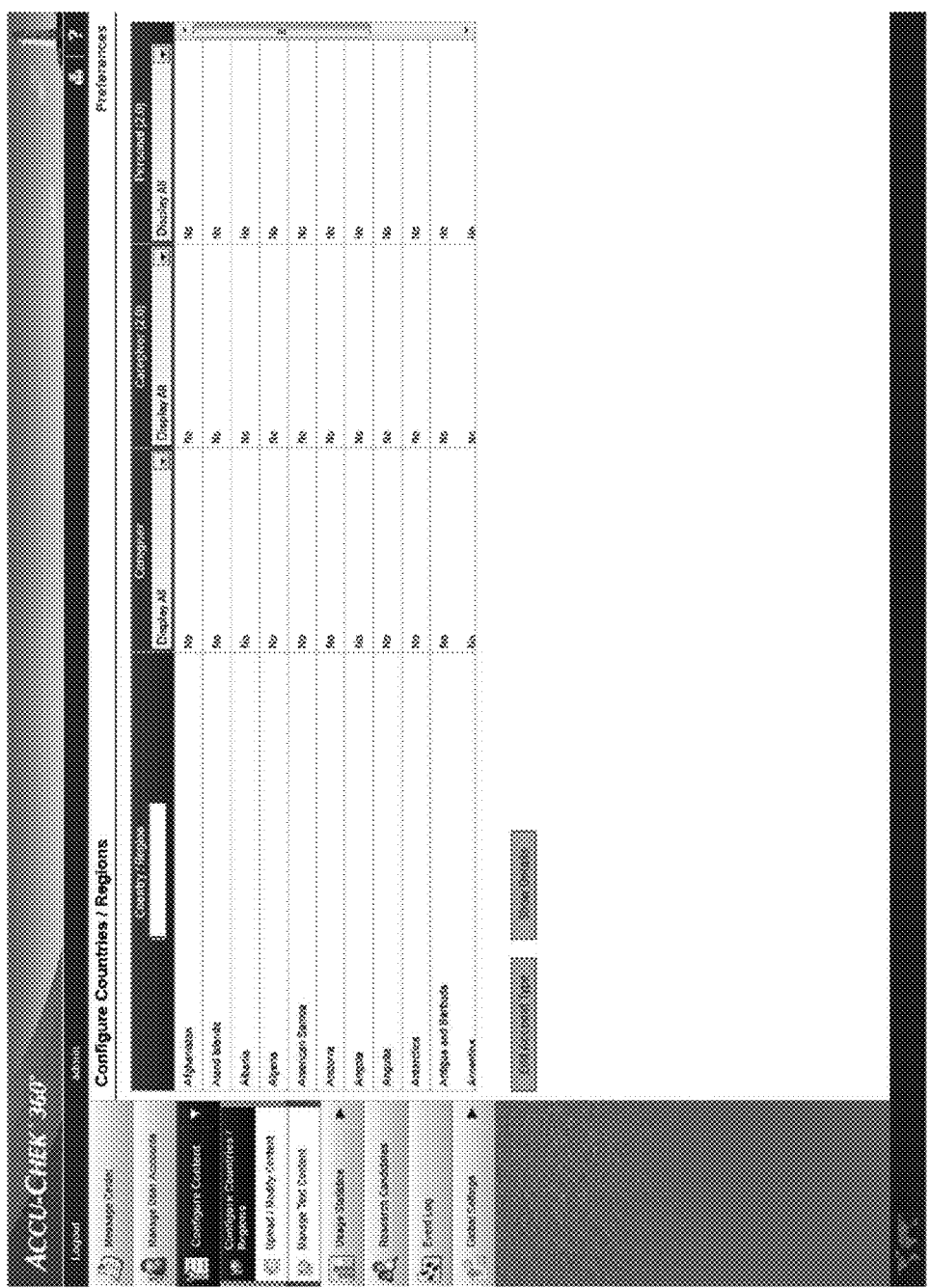

FIG. 8 generally depicts the configuration and selection of accounts assigned with countries and/or geographic regions. For example, certain healthcare provider (caregiver) accounts or patient (personal) accounts can be filtered by their association with certain countries and/or geographic regions.

Figure 9:
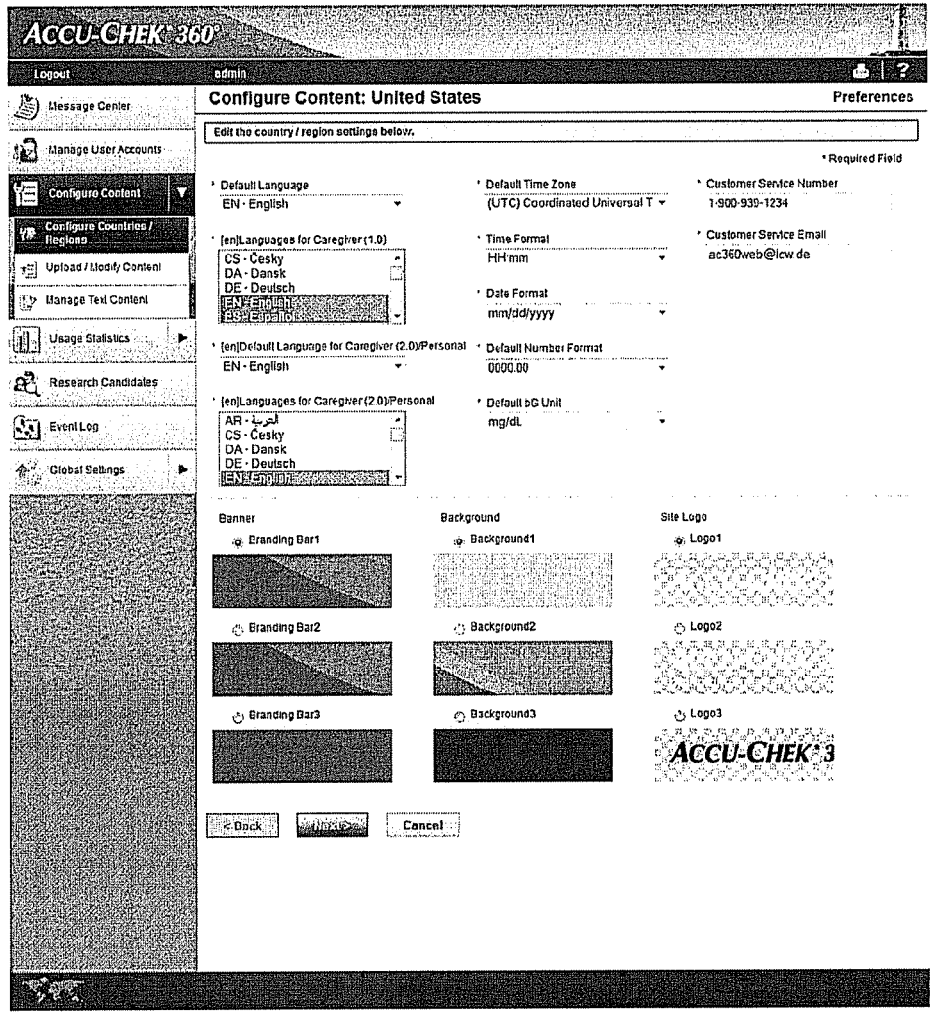
Figure 10:
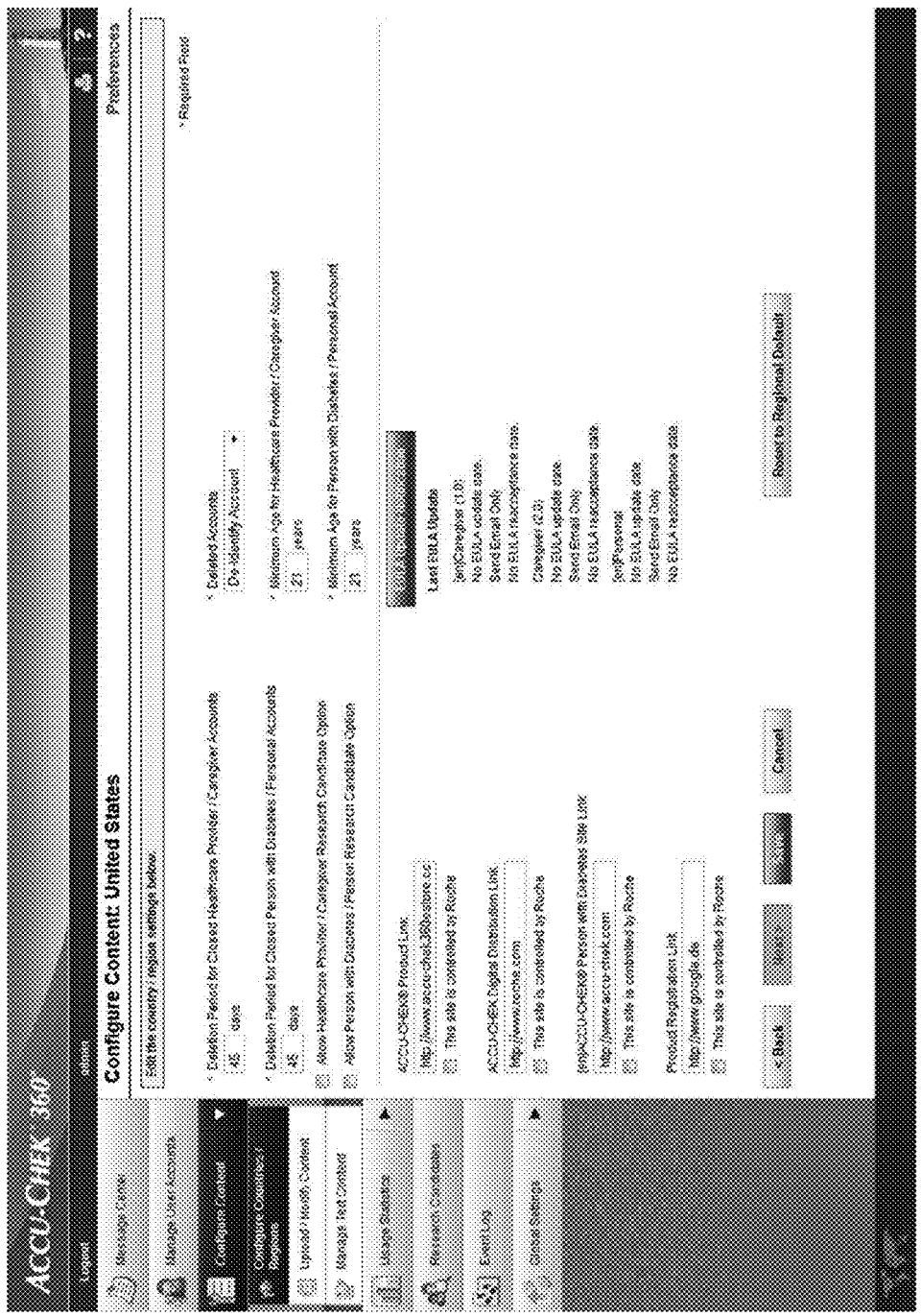

FIGS. 9 and 10 generally depict additional settings and preferences that may be associated with accounts linked with a specific country or geographic region. As shown, FIG. 9 provides a variety of regional settings such as language, time zone and time/date formats, measurement units, logos, color and background selections, and the like. FIG. 10 provides configurations for the deletion period for closed accounts, optional selection of research candidates, notations regarding minimum age requirements for account holders, and the like. FIG. 10 also provides optional information regarding medical device/product information, registration information, and End User License Agreements.

Figure 11:
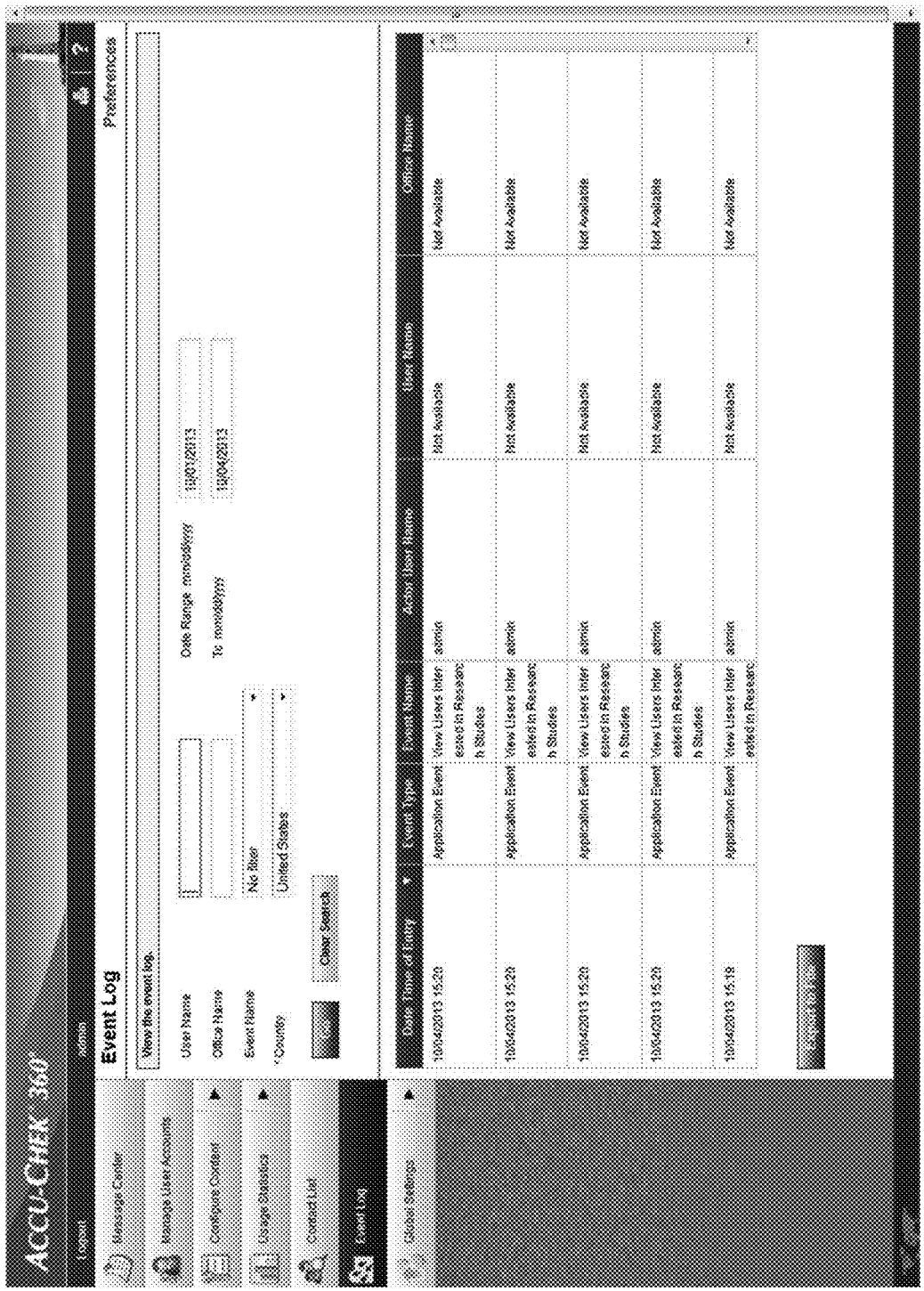

FIG. 11 provides an exemplary user interface for an event log. As shown, each event log record can include various bibliographic information, as well as description fields that display event types, names, details, user names and office names/locations.

The techniques described herein may be implemented by one or more computer programs executed by one or more processors. The computer programs include processor-executable instructions that are stored on a non-transitory tangible computer readable medium. The computer programs may also include stored data. Non-limiting examples of the non-transitory tangible computer readable medium are nonvolatile memory, magnetic storage, and optical storage.

Some portions of the above description present the techniques described herein in terms of algorithms and symbolic representations of operations on information. These algorithmic descriptions and representations are the means used by those skilled in the data processing arts to most effectively convey the substance of their work to others skilled in the art. These operations, while described functionally or logically, are understood to be implemented by computer programs. Furthermore, it has also proven convenient at times to refer to these arrangements of operations as modules or by functional names, without loss of generality.

Unless specifically stated otherwise as apparent from the above discussion, it is appreciated that throughout the description, discussions utilizing terms such as "processing" or "computing" or "calculating" or "determining" or "displaying" or the like, refer to the action and processes of a computer system, or similar electronic computing device, that manipulates and transforms data represented as physical (electronic) quantities within the computer system memories or registers or other such information storage, transmission or display devices.

Certain aspects of the described techniques include process steps and instructions described herein in the form of an algorithm. It should be noted that the described process steps and instructions could be embodied in software, firmware or hardware, and when embodied in software, could be downloaded to reside on and be operated from different platforms used by real time network operating systems.

The present disclosure also relates to an apparatus for performing the operations herein. This apparatus may be specially constructed for the required purposes, or it may comprise a general-purpose computer selectively activated or reconfigured by a computer program stored on a computer readable medium that can be accessed by the computer. Such a computer program may be stored in a tangible computer readable storage medium, such as, but is not limited to, any type of disk including floppy disks, optical disks, CD-ROMs, magnetic-optical disks, read-only memories (ROMs), random access memories (RAMs), EPROMs, EEPROMs, magnetic or optical cards, application specific integrated circuits (ASICs), or any type of media suitable for storing electronic instructions, and each coupled to a computer system bus. Furthermore, the computers referred to in the specification may include a single processor or may be architectures employing multiple processor designs for increased computing capability.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A computer-implemented method for managing accounts in a diabetes management system, comprising:
    transferring, by a device transfer component implemented on a first computing device of a first patient, blood glucose measures received from a medical data recording device via the device transfer component to a given patient account hosted by a server computer, where the device transfer component transfers the blood glucose measures without storing the blood glucose measures in a non-transitory data store of the first computing device, and where the medical data recording device is a blood glucose meter;
    receiving, by an account manager, a request to deactivate a first account of a healthcare provider, where the first account is associated with a plurality of patient accounts and the account manager is implemented as computer executable instructions executing on a computer processor of a server device, where the first patient is one of the plurality of patients having an account associated with the first account associated with the healthcare provider, and where the account of the first patient includes at least the transferred blood glucose measures;
    removing, by the account manager, access to data associated with the first account, where the data is data contained in the plurality of patient accounts associated with the first account;
    identifying, by the account manager, each of the patient accounts associated with the first account and deactivating each of the identified patient accounts associated with the first account;
    disabling, by the account manager, data transfer activities of each medical data recording device corresponding to each deactivated patient account, where the data transfer activities that are disabled are transfer of pending and future blood glucose measures;
    sending, by the account manager, an electronic notification to each patient associated with each of the identified patient accounts, where the electronic notification advises the patient that the corresponding patient account has been deactivated; and
    creating, by the account manager, an audit record in a data store, where the audit record indicates a deactivation of the first account.

2. The computer-implemented method according to claim 1, further comprising archiving data associated with each of the plurality of patient accounts for a predetermined period of time.

3. The computer-implemented method according to claim 2, wherein the predetermined period of time is associated with a geographic location for each respective patient.

4. The computer-implemented method according to claim 1, further comprising disabling, by the account manager, data synchronization functions between the first account and each of the identified patient accounts.

5. The computer-implemented method according to claim 1, further comprising disabling, by the account manager, data sharing functions between the first account and each of the identified patient accounts.

6. The computer-implemented method according to claim 1, further comprising disabling, by the account manager, data transfer activities associated with an electronic medical records system.

7. The computer-implemented method according to claim 1, further comprising authenticating, by the account manager, the request to deactivate the first account associated with the healthcare provider.

8. The computer-implemented method according to claim 1, further comprising providing confirmation, by the account manager, that the first account and the associated patient accounts are deactivated.

9. The computer-implemented method according to claim 1, further comprising creating, by the account manager, an event log record in a data store, where the event log record indicates the deactivation date of each of the identified patient accounts.

10. A computer-implemented method for managing accounts in a diabetes management system, comprising:
    transferring, by a device transfer component implemented on a computing device of a patient, blood glucose measures received from a medical data recording device via the device transfer component to a given patient account of the patient hosted by a server computer, where the device transfer component transfers the blood glucose measures without storing the blood glucose measures in a non-transitory data store of the computing device, and where the medical data recording device is a blood glucose meter;
    receiving, by an account manager, a request to deactivate the patient account of the diabetes care management system, where the account manager is implemented as computer executable instructions executing on a computer processor of the server device, and where the account of the patient includes at least the transferred blood glucose measures;
    receiving indication that the patient account is an active session;
    providing, by the account manager, a warning notification indicating that the active session of the patient account will be deactivated;
    soliciting, by the account manager, a confirmation of the request to deactivate the patient account;
    deactivating the patient account upon receipt of the confirmation of the request to deactivate the patient account;
    disabling, by the account manager, data transfer activities of the portable medical device corresponding to the deactivated patient account, where the data transfer activities that are disabled are transfer of pending and future blood glucose measures;
    sending, by the account manager, an electronic notification to the patient associated with the patient account, where the electronic notification advises the patient that the corresponding patient account has been deactivated; and
    creating, by the account manager, an audit record in a data store, where the audit record indicates the deactivation of the patient account.

11. The computer-implemented method according to claim 10, further comprising archiving data associated with the patient account for a predetermined period of time.

12. The computer-implemented method according to claim 11, where the predetermined period of time is associated with a regulatory compliance.

13. The computer-implemented method according to claim 12, where the regulatory compliance is associated with a geographic location of the patient.

14. The computer-implemented method according to claim 11, where at least a portion of the data is encrypted.

15. The computer-implemented method according to claim 10, where the request to deactivate the patient account originates from a healthcare provider.

16. The computer-implemented method according to claim 15, where the electronic notification is provided to a patient associated with the patient account.

17. The computer-implemented method according to claim 10, further comprising authenticating, by the account manager, the request to deactivate the patient account prior to deactivating the patient account.

18. The computer-implemented method according to claim 10, further comprising disabling, by the account manager, data transfer activities associated with an electronic medical records system and the patient account.

19. The computer-implemented method according to claim 10, further comprising providing, by the account manager, an option to cancel the request to deactivate the patient account.

* * * * *